United States Patent
Wood et al.

(10) Patent No.: US 11,453,850 B2
(45) Date of Patent: Sep. 27, 2022

(54) PETRI DISH WITH SINGLE-HANDED LID CONNECTION AND REMOVAL

(71) Applicant: Wisconsin Alumni Research Foundation, Madison, WI (US)

(72) Inventors: Aleksandar Relja Wood, Milwaukee, WI (US); Harpreet Singh, Oak Creek, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 258 days.

(21) Appl. No.: 16/855,062

(22) Filed: Apr. 22, 2020

(65) Prior Publication Data

US 2020/0339926 A1 Oct. 29, 2020

Related U.S. Application Data

(60) Provisional application No. 62/837,517, filed on Apr. 23, 2019.

(51) Int. Cl.
| | |
|---|---|
| *C12M 1/00* | (2006.01) |
| *C12M 1/22* | (2006.01) |
| *B65D 50/04* | (2006.01) |
| *B65D 41/06* | (2006.01) |

(52) U.S. Cl.
CPC ............. *C12M 23/10* (2013.01); *B65D 41/06* (2013.01); *B65D 50/045* (2013.01); *C12M 23/38* (2013.01)

(58) Field of Classification Search
CPC ....... C12M 23/10; C12M 23/38; B65D 41/06; B65D 50/045
USPC ............................................ 435/289.1, 305.3
See application file for complete search history.

(56) References Cited

U.S. PATENT DOCUMENTS

| | | | |
|---|---|---|---|
| 3,769,936 A | 11/1973 | Swanson et al. | |
| 4,059,198 A * | 11/1977 | Mumford | ............... B65D 41/06 215/350 |
| 8,143,053 B2 * | 3/2012 | Yerbic | .................... C12M 23/22 435/297.5 |
| 2005/0089997 A1 | 4/2005 | Minton | |
| 2006/0252299 A1 * | 11/2006 | Daykin | .................. C12M 23/10 439/409 |
| 2008/0064090 A1 * | 3/2008 | Whittlinger | ........... B01L 3/5085 435/305.3 |

FOREIGN PATENT DOCUMENTS

KR 1407246 B1 * 6/2014

* cited by examiner

*Primary Examiner* — Liban M Hassan
(74) *Attorney, Agent, or Firm* — Boyle Fredrickson, S.C.

(57) ABSTRACT

A petri dish has interlock features between the lid and dish that allow single-handed engagement of the lid with the dish by rotation, so that the lid and dish may be raised by grasping only the lid without stabilization of the dish with a second hand. Disengagement is similarly single-handed.

20 Claims, 4 Drawing Sheets

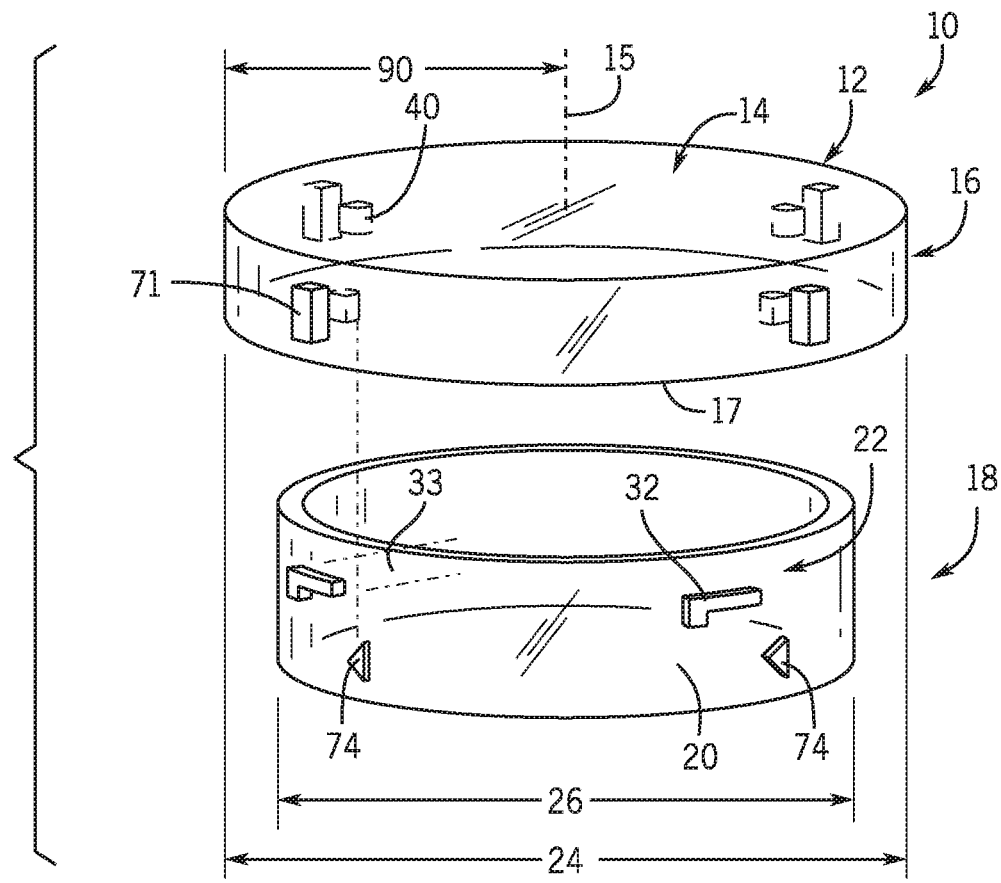
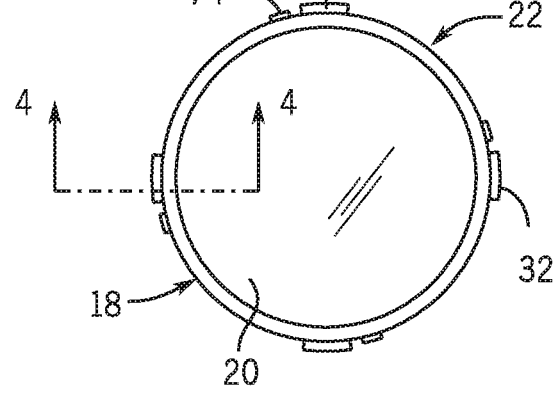
FIG. 2
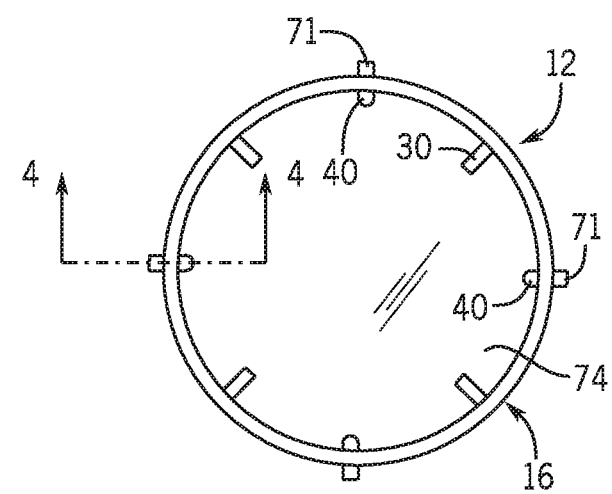
FIG. 3

PETRI DISH WITH SINGLE-HANDED LID CONNECTION AND REMOVAL

CROSS REFERENCE TO RELATED APPLICATION

This application claims the benefit of U.S. Provisional Application 62/837,517 filed Apr. 23, 2019 and hereby incorporated by reference.

BACKGROUND OF THE INVENTION

The present invention relates to a cell culture dish and lid (termed herein a petri dish) and in particular to a petri dish that provides locking features allowing the dish to be lifted by the lid and allowing single-handed lid removal.

A petri dish provides a shallow culture dish with a loosely fitting lid that can be used to culture cells such as bacteria, stem cells, and viruses as well as multicellular organisms. For this purpose, the culture dish may be partially filled with a culture medium, for example, agar and nutrient materials, and then seeded with a sample of the material to be cultured.

The lid may prevent contaminants from settling on the cultured medium from the air while providing air exchange with the contained volume, for example, by means of small standoffs attached to the under surface of the lid. The exchange of air follows a tortuous path up under the sidewalls of the lid over the rim of the culture dish past the standoffs and into the volume.

SUMMARY OF THE INVENTION

The present inventors have recognized that the ability to manipulate a petri dish by only touching the lid can provide improved resistance against contamination of the petri dish contents and simplified petri dish handling. Accordingly, the present invention allows single-handed rotation of the lid to a first position allowing the lid to be used to lift the culture dish by the lid and single-handed rotation of the lid to a second position separating the lid from the culture dish. Single-handed operation allows the user's other hand to be free, for example, for other operations such as growth media inoculation and eliminates unnecessary contact between the user's hands and the culture dish that could promote contamination.

More specifically, the present invention provides a petri dish having a dish and lid. The dish sidewalls and lid sidewalk include radially opposed ledges and teeth so that the lid may be rotated with respect to the dish to bring the ledges and teeth into axial alignment preventing removal of the lid through an abutment of the ledge and teeth or may be rotated with respect to the dish to move the ledges and teeth out of axial alignment allowing removal of the lid by allowing the ledge and teeth to pass by each other without abutment. The ledges and teeth engage to frictionally resist independent rotation of the lid and dish when the petri dish is lifted by the lid and not when the lid is supported by the dish.

It is thus a feature of at least one embodiment of the invention to provide a way of connecting the lid to the dish so that the petri dish may be moved as a unit, holding it only by the lid, simplifying the movement and reducing the risk of contamination. To this end, the lid may be connected and disconnected from the dish with one hand, something that is accomplished in part by having engaging ledges and teeth that frictionally disengage when the lid is not being lifted, allowing ready rotation of the lid with one hand either to separate or connect the dish and lid together.

The ledges and teeth can move with respect to each other without contact when the lid is supported by the dish. Similarly, the lid can rotate with respect to the dish without contact between the peripheral dish sidewalls, the ledge and an opposed sidewall, or the teeth and opposed sidewalls.

It is thus a feature of at least one embodiment of the invention to minimize rotational resistance between the lid and dish when the lid is not being lifted to promote single-handed operation.

Generally, the lid and a rim of the dish can be separated from contact without engagement of the ledges and teeth when the ledges and teeth are in axial alignment.

It is thus a feature of at least one embodiment of the invention to allow the user to grip the lid while the petri dish is on the table and rotate the lid without substantial frictional contact between the lid and dish that would require the user to grip the dish with the user's other hand.

The ledges and teeth may be spaced around the peripheral dish sidewalk and peripheral lid sidewalls respectively to allow removal of the lid and dish at a range of positions between the interlock positions.

It is thus a feature of at least one embodiment of the invention to eliminate the amount of rotation necessary to engage the lid and cover or awkward contortions of the user's hand.

The number of teeth and or number of ledges may be selected from the group consisting of 3, 4, 5, and 6.

It is thus a feature of at least one embodiment of the invention to provide for varying numbers of teeth and lids to accommodate different diameters of petri dishes.

The ledges and teeth may be in diametrically opposed pairs about the sidewalk.

It is thus a feature of at least one embodiment of the invention to minimize the necessary protrusion of the ledges and teeth. Diametric positioning reduces the impact of manufacturing tolerances on variations in the teeth and ledge overlap.

In one embodiment, the number of engaging teeth and ledges may be 4.

It is thus a feature of at least one embodiment of the invention to provide relative stability of the lid with respect to the dish along two perpendicular axes.

The ledges may provide a circumferential length of at least ⅛ inch.

It is thus a feature of at least one embodiment of the invention to provide a single-handed attachment mechanism that is resistant to minor jarring such as would separate the teeth and ledges by ensuring a minimum ledge length.

The ledges may be separated by a circumferential distance of least three times a circumferential length of the ledge.

It is thus a feature of at least one embodiment of the invention to simplify installing the lid on the dish without interference between the teeth and ledges.

The petri dish may further include rotation stops preventing rotation of the lid and dish in a first direction when the teeth are at or below a height of the ledges and the teeth are beneath respective ledges.

It is thus a feature of at least one embodiment of the invention to ensure positive alignment of the teeth and ledges by rotation of the lid until the teeth strike the stops.

A leading end of the ledge removed from the stop may have a surface angled with respect to the axis to guide the tooth to a lower surface of the ledge when the tooth strikes the leading end with rotation of the lid with respect to the dish.

It is thus a feature of at least one embodiment of the invention to promote engagement of the lid and the dish when the lid wall is not fully seated on the dish rim.

The upper surface of the lid and lower surface of the dish may provide features that center the lid and dish with respect to each other when a dish is stacked on a lid and wherein the features when engaged resist rotation between the lid and dish through abutting stops.

It is thus a feature of at least one embodiment of the invention to permit a stack of petri dishes to have their lids engaged by rotation of the lid of the uppermost petri dish translated through the centering features through the stack.

The ledge and teeth, when touching, may provide an angled interface providing a separating force between the peripheral walls of the lid and dish when the lid is pulled away from the dish producing a wedging between the ledge and teeth.

It is thus a feature of at least one embodiment of the invention to better resist relative rotation of the lid and dish when the dish is being supported by the lid, for example, during movement of the petri dish.

The outer surface of the peripheral lid sidewalk may provide tactile features indicating a location of at least one of a tooth or ledge positioned on an inner surface of the peripheral lid sidewalk in radial alignment with the tactile features. Similarly, an outer surface of the peripheral dish sidewalk may provide a marking indicating a location of at least one of a tooth or ledge positioned on an inner surface of the peripheral dish sidewalls and a rotation direction of the lid for engagement of the ledges and teeth.

It is thus a feature of at least one embodiment of the invention to provide visual and/or tactile confirmation that lid is engaged or disengaged.

The petri dish may provide for nominal diameters of 15 centimeters, 6 centimeters or 10 centimeters.

It is thus a feature of at least one embodiment of the invention to provide a system that can work with standard petri dish sizes.

The petri dish may further include standoffs attached to one of the dish or lid serving to space the upper wall from the dish rim when the lid is placed on the dish and the sidewalk may fit about the lid sidewalls when the lid is placed on the dish to allow air to flow upwardly between the lid sidewalls and dish sidewalk and between a lower surface of the upper wall and the dish rim as spaced by the standoffs.

It is thus a feature of at least one embodiment of the invention to provide a system that works with petri dishes intended to provide for air exchange with petri dish volume.

These particular objects and advantages may apply to only some embodiments falling within the claims and thus do not define the scope of the invention.

BRIEF DESCRIPTION OF THE DRAWINGS

FIG. 1 is an exploded view of a petri dish according to one embodiment of the present invention showing the lid positioned above the dish prior to engagement and showing relative alignment of inwardly facing teeth on the lid with respect to outwardly fixing ledges on the dish;

FIG. 2 is a top plan view of the dish of FIG. 1 showing the projection of the ledges radially outward in one embodiment;

FIG. 3 is a bottom plan view of the lid of FIG. 1 showing the inward projection of the teeth corresponding to the ledges;

DETAILED DESCRIPTION OF THE PREFERRED EMBODIMENT

Figure 4:
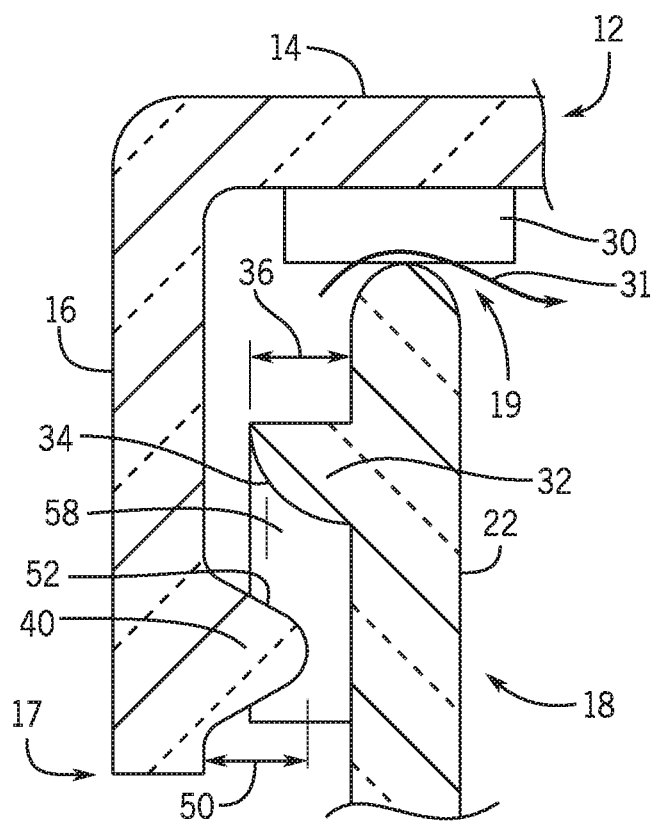
FIG. 4 is a cross-section taken along lines 4-4 of FIGS. 2 and 3 when the lid and dish are assembled showing relative overlap of the ledge and teeth and their wedging interconnection.

Referring now to FIG. 1, a petri dish 10 may provide a lid 12 having a top circular wall 14 generally radially symmetric about a center axis 15, for example, in the form of a circular disk. Downwardly extending lid sidewalls 16 attach at the periphery of the top wall 14 and terminate at a lower circular rim 17.

The lid 12 may provide a releasable cover for a dish 18 having a bottom circular wall 20 also generally radially symmetric about the center axis 15 and also in the form of a circular disk. The bottom wall 20 attaches at its periphery to upstanding dish sidewalls 22 terminating at a dish rim 19.

The axis 15 is generally perpendicular to the broad faces of the top circular wall 14 and bottom circular wall 20 and defines the direction along which the lid 12 and dish 18 are assembled or removed from each other.

An inner diameter 24 of the lid sidewalls 16 will be larger than an outer diameter 26 of the dish sidewalls 22 so that the lid 12 and dish 18 may be assembled without interference between these surfaces and further may permit air flow between the inside surface of the lid sidewalk 16 and the outside surface of the dish sidewalk 22.

Referring momentarily to FIG. 4, narrow standoffs 30 may be attached to the underside of the top circular wall 14 at various locations about the periphery of the top wall 14 and above the rim 19 to space the top circular wall 14 away from the rim 19 when the lid 12 and dish 18 are assembled. The standoffs 30 may have a height measured along the axis 15 of 0.2 millimeters in one embodiment.

The difference in diameter between the sidewalls of the lid 12 and dish 18 and the standoffs 30 allow air flow 31 into and out of an enclosed volume formed by the connection of the lid 12 and dish 18. The rim 19 may be upwardly rounded and the corresponding lower surface of the standoffs 30 may be flat or rounded to reduce the contact area between the rim 19 and standoffs 30 for reduced risk of adhesion and possible friction reduction.

Referring again also to FIG. 1, it will be appreciated that the clearances described between the walls 22 and 16 and the small contact area between the standoff 30 and the rim 19 allow the lid 12 to be rotated about axis 15 with respect to the dish 18 without moving the dish 18. More specifically, the force of torsion from frictional contact between the dish 18 and the lid 12 under the weight of the lid 12 is adjusted to be less than countervailing torsion caused by frictional contact between the dish 18 (when empty) and the supporting surface of a table under the weight of the lid 12 and dish 18. In this regard, the coefficient of friction between a table and the dish 18 may be assumed to be between 0.3 and 0.5 $\mu_s$ being the static coefficient of friction between polystyrene and steel. Thus, it will be appreciated, that the lid 12 may be rotated single-handedly without stabilizing the dish 18 with the other hand when the lid 12 is resting on the dish 18 and the dish 18 is resting on a standard table. Alternatively, the lid 12 may be lifted slightly to remove contact between the lid 12 and the dish 18 during this rotation. In this regard, when the lid 12 is resting on the dish 18, the teeth 40 and ledges 32 may be removed from contact with each other. More generally the inner surfaces of the teeth 40 and of the ledges 32 may be free from contact with the opposed sidewalls 22 and 16 during isocentric rotation of the lid 12 about the dish 18 to further reduce frictional contact at this time.

Referring now to FIGS. 1, 2, 4, and 5, the ledges 32 extending radially from the outside surface of the sidewalk 22 of the dish 18, for example, as shown in FIG. 2, are equally spaced around the periphery of the dish 18, at 90 degrees about axis 15. Each of the ledges 32 extends a circumferential angular extent 33 (shown in FIG. 1) and extends radially by a projection distance 36 (shown in FIG. 4). In one example this projection distance 36 may be 1.2 millimeters. As noted, projection distance 36 is such that when the lid 12 is on the dish 18 and centered, the inner surface of the sidewall 16 need not touch the ledge 32.

The height of the ledge 32 below the rim 19 will be such that it is above the height of the tooth 40 when the lid 12 is resting on the dish 18.

A left edge of the ledge 32 may connect or be adjacent to a downwardly extending stop 38 having a substantially equal projection distance 36 and an arbitrary height sufficient to block circumferential motion of the tooth 40 as will be described. In one embodiment, the stop 38 may present an outwardly convex hemi cylindrical surface.

Figure 5:
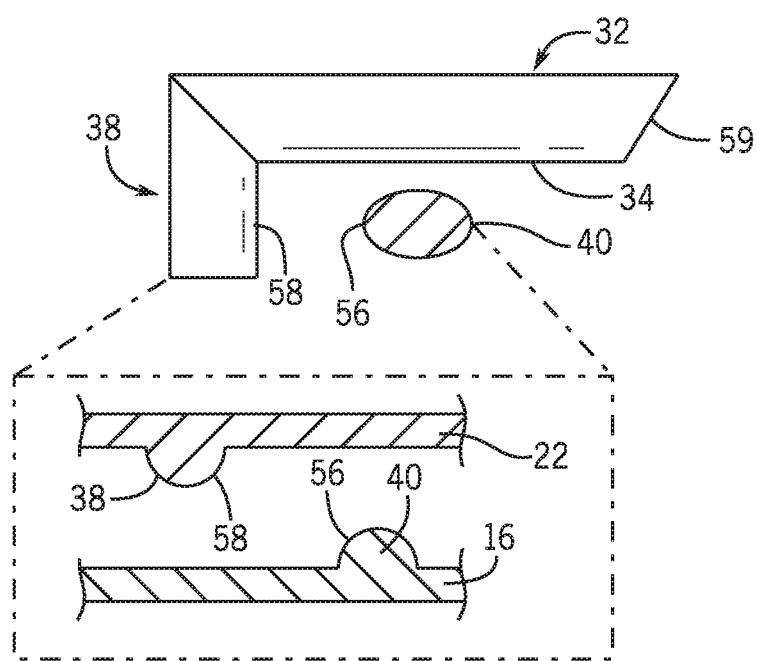
FIG. 5 is a fragmentary elevational view of the outer surface of a sidewall of the dish showing the ledge and stop superimposed on a cross-section of the tooth positioned for engagement, and providing an inset showing a plan cross-section of the stop and tooth.

Referring now to FIGS. 1, 3, and 5, the teeth 40 extending radially inward from the inner surface of the walls 16 of the lid 12, for example, as shown in FIG. 2, may also be equally spaced around the periphery of the lid 12 at 90° about axis 15 to match the spacing of the ledges 32. Each of the teeth 40 may have a projection distance 50 radially inward. The projection distance 50 is such that when the lid 12 is on the dish 18 and centered about the axis 15, the inner surface of the teeth 40 need not touch the outer surface of the sidewall 22. Nevertheless, the teeth 40 when aligned with the ledges 32 angularly about the axis 15 overlap in directions parallel to the axis 15 (whether the lid 12 is centered on the dish 18 or not) so long as the lid 12 is resting on the dish 18. In this configuration, when the lid 12 is raised, interference between the tooth 40 and the ledge 32 cause the dish 18 to rise with the lid 12 in an engaged state. In this regard, a lower surface 34 of the ledge 32 and upper surface 52 of the tooth 40 may be beveled or tipped with respect to a radial direction to provide a wedging action with their engagement forcing the tooth 40 outward and the ledge 32 inward to increase resistive forces and better prevent rotation between the lid 12 and dish 18 in this engaged lifted state.

Referring to FIG. 5, when the lid 12 is rotated with respect to the dish 18 (clockwise as viewed from above) the tooth 40 may engage the stop 38 holding the tooth 40 beneath the ledge 32. This allows ready alignment of the tooth 40 with the ledge 32 by rotation until engagement of the tooth 40 and stop 38 causing the dish 18 to rotate with the lid 12. At that point engagement can be assured and the lid 12 may be lifted.

A leading surface 56 of the tooth 40 facing the stop 38 and a trailing surface 58 of the stop 38 facing the tooth 40 may also have wedge shapes to push the tooth 40 outward and the stop 38 inward with engagement creating additional pressure to prevent accidental dislodgment during lifting of the petri dish 10 by the lid 12.

Referring still to the FIG. 5, the distance that the tooth 40 may drop below the ledge 32 is limited by engagement between the standoff 30 of the lid 12 and the upper rim 19 thus limiting the necessary height of the stop 38 to ensure stopping of the tooth 40. A leading edge 59 of the ledge 32 may be beveled so that when the lid 12 is not fully engaged with the standoffs 30 against the rim 19, the tooth 40 will be guided downward beneath the ledge 32.

Figure 6:
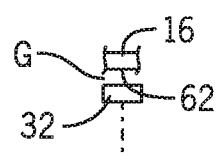
FIG. 6 is a diagrammatic representation of one positioning of the teeth and ledges providing a single pair of opposed corresponding ledges and a spacing from the inner surface of the sidewalls of the lid.
Figure 7:
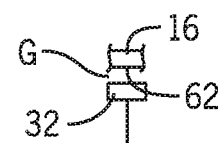
FIG. 7 is a figure similar to FIG. 8 showing three equally angularly spaced ledges.

Referring now to FIG. 6, one pair of ledges 32 may be diametrically opposed across axis 15, for example, in an embodiment having only two ledges 32. In this diametric arrangement, a gap (G) between the outer surface of the ledges 32 and an inner surface 62 of the sidewalk 16 (promoting free rotation of the lid 12 with respect to the dish 18) will allow lateral motion of the lid 12 with respect to the dish 18 of a distance 2G. This possible lateral motion requires radial overlap between the projection distances 36 and 50 of an amount more than 2G. In contrast, and referring to FIG. 7, with a non-diametric arrangement of the ledges 32 at every 120°, a similar gap G between the outer surface of the ledges 32 and the inner surface 62 of the sidewalk 16 will allow lateral motion of the lid 12 with respect to the dish 18 of 3G requiring an increase in overlap between the projection distances 36 and 50 (effectively a reduction in the gap G) thus requiring more exacting tolerances. It will he understood that the gap G may alternatively be measured between the inner surface of the teeth 40 and the outer surface of the sidewalls 22 and may usefully be the smaller of such measurements.

Figure 8:
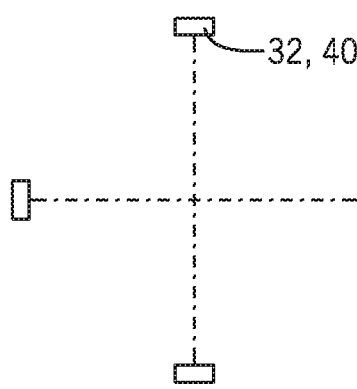
FIG. 8 is a figure similar to FIGS. 6 and 7 showing four equally spaced ledges.

In one embodiment, shown in FIG. 8, a set of two pairs of diametrically opposed ledges 32 with corresponding teeth 40 (not shown) may be used, each pair along perpendicular axes. This provides the benefit of lower tolerance in the fabrication of the petri dish 10, per the discussion of FIG. 3, and reduces rocking of the lid 12 with respect to the dish 18 around axes in the plane of the lid, for example, the axis between the ledges 32 of FIG. 6.

Figure 9:
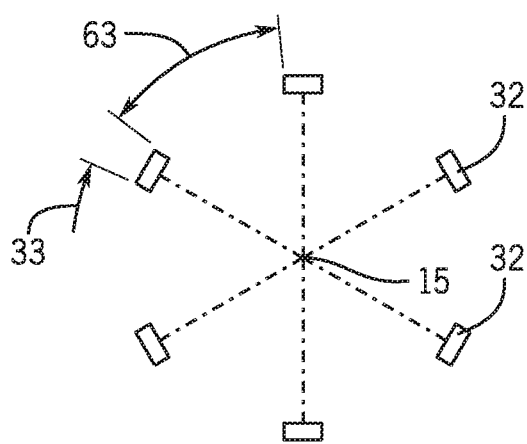
FIG. 9 is a figure similar to that of FIGS. 6, 7, and 8 showing six equally spaced ledges.

Referring to FIG. 9, in one embodiment six ledges 32 may be positioned at equal angular spacing of 60 degrees may be used particularly for larger petri dishes 10 where more stability between the lid 12 and dish 18 may be desired. Generally, the angular span 33 of the ledges 32 will be less than one third and preferably less than one fourth the angular separation 63 about axis 15 of adjacent ledges 32 along a circumferential direction. The circumferential length of the ledge 32 may be more than ⅛ of an inch and the angular extent typically greater than 3°. This makes it easier to assemble the lid 12 and dish 18 without concern about possible interference between the ledges 32 and teeth 40.

Figure 10:
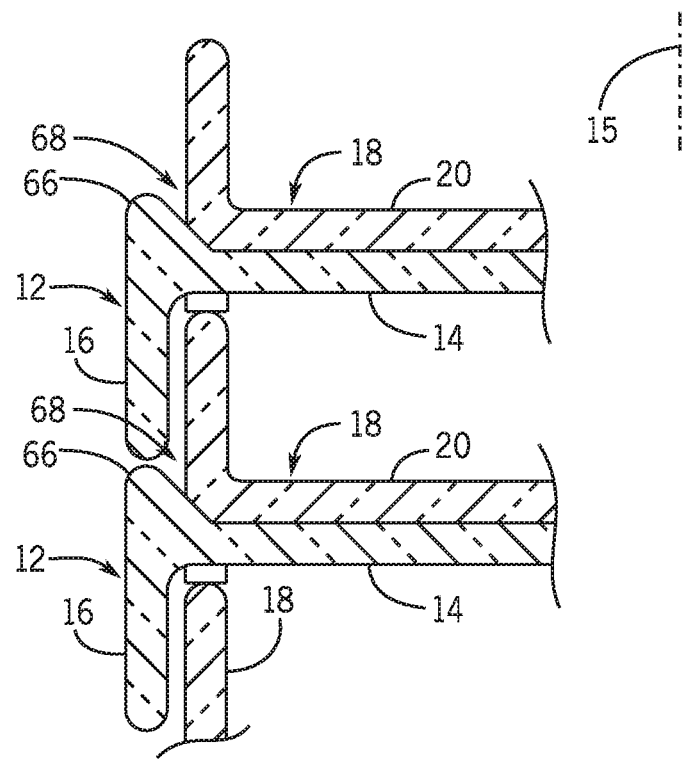
FIG. 10 is a fragmentary elevational cross-section through a stack of assembled lids and dishes showing stack alignment ridges with anti-rotation features.
Figure 11:
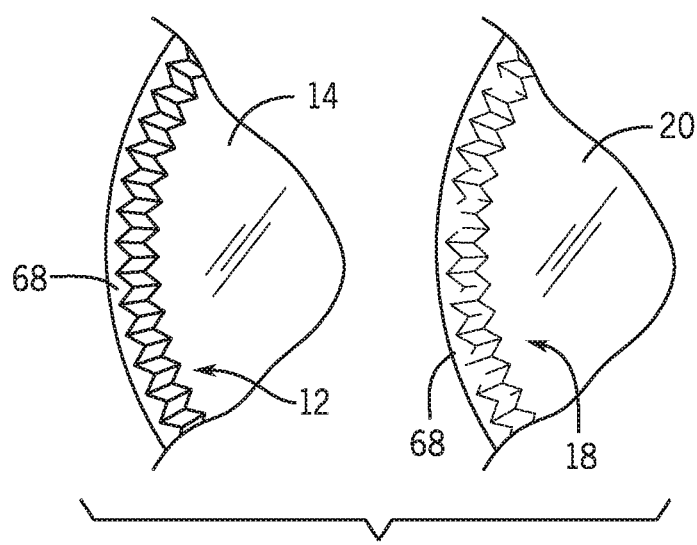
FIG. 11 is a fragmentary bottom plan view of a dish and top plan view of a lid (displaced laterally for clarity) showing the stack alignment ridges and anti-rotation features of FIG. 10.

Referring now to FIG. 10, an upper surface of the lid 12 may provide for a circular rim 66 projecting upward there-from and concentric about axis 15 that surrounds and engages on its inner surface the outer periphery of the bottom wall 20 of the dish 18 so as to align a stack of alternate dishes 18 and lids 12 for improved stability. The interface between the rim 66 and outer periphery of the bottom wall 20 may provide for interengaging teeth 68 also canted with respect to axis 15 to assist in the centering of the stacked elements as they are stacked and to resist relative rotation between a dish 18 on top of a lid 12. In this way, when the lids 12 and dishes 18 are arranged in a stack, rotation of the uppermost lid 12 may be communicated through the stack, for example, to engage all of the lids 12 with their respective dishes 18.

Importantly, these features need not affect (protrude from) the lower surface of the bottom wall 20 of the dish 18 such as might adversely reduce its frictional contact with the supporting surface of a table or the like during use of the dish 18. Any teeth in the sidewall 22 may be slightly elevated away from the bottom of the bottom wall 20 for this reason.

Referring again to FIG. 1, positioned radially in alignment with each of the teeth 40 but on the outside of the sidewall 16 may be a tactile feature 71, for example, a protruding bar allowing the user to quickly identify the location of the teeth by feel. A fiducial arrow 74 (which may also be a tactile embossment) may be positioned on the outer surface of the sidewall 22 below the height of the sidewall 16 when the lid 12 is engaged with the dish 18 and may indicate a direction of engagement (rotation of the lid 12) so that the tooth 40 comes into engagement with the stop 38 beneath the ledge 32. During assembly of the lid 12 with a dish 18, the tactile feature 71 and fiducial arrow 74 may be used to roughly align the teeth 40 and ledges 32 to ensure no interference between the tooth 40 and the ledge 32 during engagement of the lid 12 with the dish 18 and so that they may be easily engaged by rotation.

The lid 12 and dish 18 and their described features may be constructed of a variety of materials, for example, including polymer materials and glass and may desirably be transparent. An example polymer is polystyrene, permitting ready fabrication of the petri dish 10 by injection molding, although other materials are also contemplated. The lid 12 and dish 18 may be treated, for example, with surface treatments such as a poly-D-lysine or other treatments known in the art for constructing petri dishes. The invention contemplates that the petri dish 10 may be empty or may include nutrient materials such as an agar-based material, water or the like.

The invention contemplates a variety of sizes of petri dishes corresponding to the standards existing in the industry, for example, including nominal dish diameters of 33 millimeters, 54 millimeters, 83 millimeters, and 136 millimeters among others as shown in FIG. 1 by diameter 90. A typical lid height for a 50 millimeter diameter petri dish may be 8.2 millimeters and a dish height of 14 millimeters.

Friction and frictional engagement as used herein means a three that resists sliding between surfaces that may slide with respect to each other and may be distinguished, for example, from abutting surfaces that cannot move without distortion of the surfaces.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A petri dish comprising:
a dish providing a bottom wall with peripheral dish sidewalls extending upward from the bottom wall to a dish rim to define a dish volume; and
a lid providing a cover to the dish and having an upper wall with peripheral lid sidewalk extending downward from the upper wall to a lid rim;
wherein one of the peripheral dish sidewalls and peripheral lid sidewalk include ledges extending radially in a first direction and another of the peripheral dish sidewalk and peripheral lid sidewalk includes teeth extending radially in a second direction opposite the first direction;
wherein the lid is adapted to be rotated with respect to the dish to bring the ledges and teeth into a locked state with axial alignment of teeth below the ledges preventing removal of the lid through an abutment of the ledges and teeth, and the lid is adapted to be rotated with respect to the dish to move the ledges and teeth to an unlocked state out of axial alignment allowing removal of the lid by allowing the ledges and teeth to pass by each other during removal without abutment; and wherein the lid and dish are adapted to rotate with respect to each other into or out of the locked state and without interference between the lid and dish when the teeth are below the ledges.

2. The petri dish of claim 1 wherein the ledges and teeth do not contact each other when the lid is supported by the dish.

3. The petri dish of claim 1 wherein the lid is adapted to rotate with respect to the dish without contact between the peripheral dish sidewalls and the peripheral lid sidewalk when the lid is on the dish.

4. The petri dish of claim 1 wherein the lid is adapted to rotate with respect to the dish without contact between the teeth and opposed sidewalls when the lid on the dish.

5. The petri dish of claim 1 wherein the lid is adapted to rotate with respect to the dish without contact between the ledges and opposed sidewalk when the lid is on the dish.

6. The petri dish of claim 1 wherein the lid and a rim of the dish can be separated from contact to remove the lid without engagement of the ledges and teeth when the ledges and teeth are not in axial alignment.

7. The petri dish of claim 1 wherein the ledges and teeth are spaced around the peripheral dish sidewalls and peripheral lid sidewalls respectively to allow removal of the lid and dish at a range of positions between the positions of angular alignment.

8. The petri dish of claim 7 wherein a number of teeth and/or number of ledges is selected from the group consisting of 3, 4, 5, and 6.

9. The petri dish of claim 7 wherein the ledges and teeth are in diametrically opposed pairs about the sidewalls.

10. The petri dish of claim 8 wherein the number of engaging teeth and ledges is 4.

11. The petri dish of claim 1 wherein ledges provide a circumferential length of at least ⅛ inch.

12. The petri dish of claim 1 wherein the ledges are separated by a circumferential distance of at least three times a circumferential length of the ledges.

13. The petri dish of claim 1 further including rotation stops preventing rotation of the lid and dish in only a first direction when the teeth are at or below a height of the ledges.

14. The petri dish of claim 13 wherein a leading end of the ledges opposite the rotational stops has a surface angled to guide the teeth to a lower surface of the ledge when a tooth strikes the leading end with rotation of the lid with respect to the dish.

15. The petri dish of claim 1 wherein at least one of an upper surface of the lid and a lower surface of the dish are circular and provides outwardly extending projections with equal angular spacing that center the lid and dish with respect to each other when a dish is stacked on a lid and wherein the outwardly extending projections when engaged resist rotation between the lid and dish through abutting stops.

16. The petri dish of claim 1 wherein the ledges and teeth, when touching, provide an angled interface providing a separating force between the peripheral walls when the lid is pulled away from the dish producing a wedging between the ledges and teeth.

17. The petri dish of claim 1 wherein an outer surface of the peripheral lid sidewalls provide tactile features indicating a location of at least one of a tooth or ledge positioned on an inner surface of the peripheral lid sidewalls in radial alignment with the tactile features.

18. The petri dish of claim 1 wherein an outer surface of the peripheral dish sidewalk provides a marking indicating a location of at least one of a tooth or ledge positioned on an inner surface of the peripheral dish sidewalls and a rotation direction of the lid for engagement of the ledges and teeth.

19. The petri dish of claim 1 wherein a nominal diameter of the petri dish is selected from the group consisting of 3.5 centimeters, 6 centimeters, and 10 centimeters.

20. The petri dish of claim 1 further including standoffs attached to one of the dish or lid and spacing the upper wall from the dish rim when the lid is placed on the dish;

wherein the dish sidewalls #it about the lid sidewalls when the lid is placed on the dish to allow air flow upwardly between the lid sidewalk and dish sidewalls and between a lower surface of the upper wall and the dish rim as spaced by the standoffs.

\* \* \* \* \*